United States Patent [19]

Manning et al.

[11] 4,399,125
[45] Aug. 16, 1983

[54] NOVEL ANTAGONISTS OF THE ANTIDIURETIC ACTION OF ARGININE VASOPRESSIN

[76] Inventors: Maurice Manning, 3741 Driftwood, Toledo, Ohio 43614; Wilbur H. Sawyer, #12 Warnke La., Scarsdale, N.Y. 10583

[21] Appl. No.: 322,071

[22] Filed: Nov. 16, 1981

Related U.S. Application Data

[63] Continuation-in-part of Ser. No. 247,008, Mar. 24, 1981, Pat. No. 4,367,225.

[51] Int. Cl.³ ...................... A61K 37/00; C07C 103/52
[52] U.S. Cl. .............................. 424/177; 260/112.5 R
[58] Field of Search ................... 260/112.5 R; 424/177

[56] References Cited

U.S. PATENT DOCUMENTS

| | | | |
|---|---|---|---|
| 3,371,080 | 2/1968 | Boissonnes et al. | 260/112.5 R |
| 3,415,805 | 12/1968 | Siedel et al. | 260/112.5 R |
| 3,418,307 | 12/1968 | Boissonnes et al. | 260/112.5 R |
| 3,454,549 | 7/1969 | Boissonnes et al. | 260/112.5 R |
| 3,497,491 | 2/1970 | Zavral et al. | 260/112.5 R |
| 4,148,787 | 4/1979 | Mulder et al. | 260/112.5 R |

OTHER PUBLICATIONS

J. Med. Chem. 1981, 24, 701–706; 1980, 23, 364–368; 1978, 21, 313–315; 1975, 18, 1022–1024; 1978, 21, 850–853; 1974, 17, 250–252.

J. Pharm. & Exper. Therap. 174, 1970, 541–549; 1975, 196, 746–757.

Science 161, 1968, 280–281; 212, 1981, 49–51.

Primary Examiner—Delbert R. Phillips
Attorney, Agent, or Firm—Emch, Schaffer & Schaub Co.

[57] ABSTRACT

Compounds acting as antagonists of the antidiuretic activity of arginine vasopressin are those of the formula

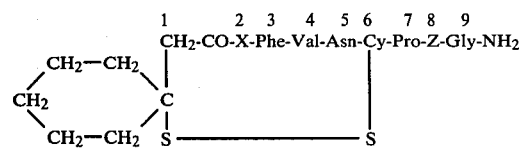

wherein X is D-Phe, D-Val, D-Leu, D-Ile, D-Arg, D-norvaline, D-norleucine, D-cyclohexylalanine, D-α-aminobutyric acid, D-threonine or D-methionine and Z is D- or L-Arg.

13 Claims, No Drawings

NOVEL ANTAGONISTS OF THE ANTIDIURETIC ACTION OF ARGININE VASOPRESSIN

The invention described herein was made in the course of work under a grant or award from the Department of Health and Human Services.

REFERENCE TO RELATED APPLICATION

This is a continuation-in-part of Manning et al., Ser. No. 247,008, filed Mar. 24, 1981, now U.S. Pat. No. 4,367,225 issued Jan. 4, 1983.

BACKGROUND OF THE INVENTION

This invention relates to novel peptides which antagonize the antidiuretic and/or vasopressor action of arginine vasopressin in vivo.

PRIOR ART STATEMENT

Attempts to develop clinically useful synthetic antagonists of in vivo antidiuretic and/or vasopressor responses to arginine vasopressin, the antidiuretic hormone (ADH), have led to the synthesis and pharmacological evaluation of hundreds of analogs of the neurohypophysial peptides, oxytocin and vasopressin.

Analogs which can effectively antagonize in vivo vasopressor responses to ADH have been reported by Dyckes et al., *J. Med. Chem.*, vol. 17 (1974) at 250; Manning et al., *J. Med. Chem.*, vol. 20 (1977) at 1228; Bankowski et al., *J. Med. Chem.*, vol. 21 (1978) at 850; Kruszynski et al., *J. Med. Chem.*, vol. 23 (1980) at 364 and Lowbridge et al., *J. Med. Chem.*, vol. 21 (1978) at 313, herein incorporated by reference.

Kruszynski et al. reported that [1-($\beta$-mercapto-$\beta$,$\beta$-cyclopentamethylenepropionic acid), 2-(O-methyl)-tyrosine]arginine vasopressin and [1-$\beta$-mercapto-$\beta$,$\beta$-cyclopentamethylenepropionic acid]-arginine vasopressin are potent vasopressor antagonists, which also have very low antidiuretic potency.

Manning et al. (1977) described the synthesis of [1-deaminopenicillamine, 4-valine, 8-D-argine] vasopressin and Lowbridge et al. the synthesis of [1-($\beta$-mercapto-$\beta$,$\beta$-cyclopentamethylenepropionic acid), 4-valine, 8-D-arginine] vasopressin. Both of these compounds have weak antidiuretic activity and are potent antagonists of the vasopressor response to AVP.

Analogs of vasopressin or oxytocin which antagonize antidiuretic responses to ADH have been reported by Chan et al., *Science*, vol. 161 (1968) at 280 and *J. Pharmacol. Exp. Ther.*, vol. 174 (1970) at 541 and vol. 196 (1976) at 746; Nestor et al., *J. Med. Chem.*, vol. 18 (1975) at 1022 and Larsson et al., *J. Med. Chem.*, vol. 21 (1978) at 342, herein incorporated by reference. None of the compounds reported has been pharmacologically or clinically useful as an antidiuretic antagonist.

The synthesis and evaluation of vasopressin analogs, incorporating etherified tyrosine at the 2-position, valine at the 4-position and D- or L-Arg at the 8-position, which antagonize the anti-diuretic action ADH in vivo have been reported by Sawyer et al., *Science*, vol. 212 (1981) at 49 and by Manning et al., *J. Med. Chem.*, vol. 24 (1981) at 701, herein incorporated by reference.

Synthetic vasopressins have been disclosed in the following U.S. patents:
- U.S. Pat. No. 3,371,080—Boissonnas et al.
- U.S. Pat. No. 3,415,805—Siedel et al.
- U.S. Pat. No. 3,418,307—Boissonnas et al.
- U.S. Pat. No. 3,454,549—Boissonnas et al.
- U.S. Pat. No. 3,497,491—Zaoral
- U.S. Pat. No. 4,148,787—Mudler et al.

Of these references, Boissonnas et al., '080 discloses that 2-phenylalanine-8-ornithine vasopressin has a vasoconstrictive action equal to that of natural vasopressins but low antidiuretic activity. The remaining references disclose synthetic vasopressins having high or relatively specific antidiuretic activity.

Synthetic modifications of oxytocin are disclosed by Manning in U.S. Pat. Nos. 3,691,147 and 3,700,652.

It is therefore apparent that there is a continuing need for the development of pharmacologically and clinically effective antagonists of the antidiuretic action of arginine vasopressin.

OBJECT OF THE INVENTION

It is the object of the invention to provide antagonists of the antidiuretic action of ADH, which are effective in vivo.

SUMMARY OF THE INVENTION

This invention relates to novel antagonists of the antidiuretic action of ADH, which are compounds of Formula I,

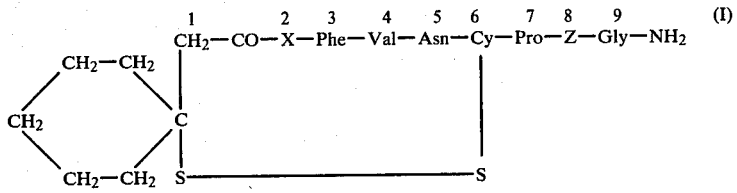

wherein X is D-Phe, D-Val, D-Leu, D-Ile, D-Arg, D-norvaline, D-norleucine, D-cyclohexylalanine, D-$\alpha$-aminobutyric acid, D-threonine or D-methionine and Z is D- or L-Arg.

This invention further relates to a method for antagonizing the in vivo response to ADH, comprising administering to an animal being treated an amount of one of the foregoing compounds, in admixture with a physiologically and pharmaceutically acceptable carrier, effective to antagonize the antidiuretic response to ADH.

DETAILED DESCRIPTION

Compounds provided in accordance with the invention are derivatives of arginine vasopressin (AVP). Amino acids are in the L-form unless otherwise indicated. The correlation between full names and abbreviations is: dAVP, 1-deamino-arginine vasopressin; dPAVP, [1-deaminopenicillamine]-arginine vasopressin; d(CH$_2$)$_5$AVP, [1-($\beta$-mercapto-$\beta$,$\beta$-cyclopentamethylenepropionic acid)]-arginine vasopressin; dVDAVP, 1-deamino[4-valine, 8-D-arginine] vasopressin; dPVDAVP, [1-deaminopenicillamine, 4-valine, 8-D-arginine]vasopressin; d(CH$_2$)$_5$VDAVP, [1-($\beta$-mercapto-$\beta$,$\beta$-cyclopentamethylenepropionic acid), 4-valine, 8-D-arginine] vasopressin; dTyr(Me)AVP, 1- deamino[2-(O-methyl)-tyrosine]-arginine vasopressin; dPTyr(Me)AVP, [1-deaminopenicillamine, 2-(O-methyl)tyrosine]-arginine vasopressin; d(CH$_2$)$_5$Tyr(Me)VDAVP, [1-($\beta$-mercapto-$\beta$,$\beta$-cyclopentamethylenepropionic acid), 2-O-methyltyrosine, 4-valine, 8-D-arginine] vasopressin; d(CH$_2$)$_5$ D-Tyr VDAVP, [1-($\beta$-mercapto-$\beta$,$\beta$-cyclopentamethylenepropionic acid), 2-D-tyrosine, 4-valine, 8-D-arginine] vasopressin; d(CH$_2$)$_5$ D-Tyr VAVP, [1-($\beta$-mercapto-$\beta$,$\beta$-cyclopentamethylenepropionic acid), 2-D-tyrosine, 4-valine]-arginine vasopressin; d(CH$_2$)$_5$D-Phe$^2$ VDAVP, [1-($\beta$-mercapto-$\beta$,$\beta$-cyclopentamethylenepropionic acid), 2-D-phenylalanine, 4-valine, 8-D-arginine] vasopressin; d(CH$_2$)$_5$ D-Phe VAVP, [1-($\beta$-mercapto-$\beta$,$\beta$-cyclopentamethylenepropionic acid), 2-D-phenylalanine, 4-valine]-arginine vasopressin; d(CH$_2$)$_5$ [Gly$^2$] VAVP, [1-($\beta$-mercapto-$\beta$,$\beta$-cyclopentamethylenepropionic acid), 2-glycine, 4-valine]-arginine vasopressin; d(CH$_2$)$_5$[D-Ala$^2$] VAVP, [1-($\beta$-mercapto-$\beta$,$\beta$-cyclopentamethylenepropionic acid), 2-D-alanine, 4-valine]-arginine vasopressin; d(CH$_2$)$_5$ [D-Val$^2$] VAVP [1-($\beta$-mercapto-$\beta$,$\beta$-cyclopentamethylenepropionic acid), 2-D-valine, 4-valine]-arginine vasopressin; d(CH$_2$)$_5$ [D-Leu$^2$] VAVP, [1-($\beta$-mercapto-$\beta$,$\beta$-cyclopentamethylenepropionic acid), 2-D-leucine, 4-valine]-arginine vasopressin; d(CH$_2$)$_5$ [D-Ile$^2$] VAVP, [1-($\beta$-mercapto-$\beta$,$\beta$-cyclopentamethylenepropionic acid), 2-D-isoleucine, 4-valine]-arginine vasopressin; and d(CH$_2$)$_5$ [D-Arg$^2$] VAVP, [1-($\beta$-mercapto-$\beta$,$\beta$-cyclopentamethylenepropionic acid), 2-D-arginine, 4-valine]-arginine vasopressin.

The active peptides were synthesized by solid phase synthesis as described by Bankowski et al. (1978), supra; Merrifield, J. Am. Chem. Soc., vol. 85 (1963) at 2149 and Biochemistry, vol. 3 (1964) at 1385; Manning, J. Am. Chem. Soc., vol. 90 (1968) at 1348; Manning et al., J. Med. Chem., vol. 19 (1976) at 376; Lowbridge et al., J. Med. Chem., vol. 20 (1977) at 1173; Manning et al., J. Med. Chem., vol. 16 (1973) at 975; Kruszynski et al. (1980), supra; Sawyer et al., (1981), supra; or Manning et al. (1981), supra.

Initial attempts to design an antagonist of the antidiuretic response to arginine vasopressin (AVP) including synthesis of [1-deaminopenicillamine, 4-valine, 8-D-arginine] vasopressin (dPVDAVP) by Manning et al. (1977), supra, and of [1-($\beta$-mercapto-$\beta$,$\beta$-cyclopentamethylenepropionic acid), 4-valine, 8-D-arginine] vasopressin (d(CH$_2$)$_5$VDAVP), Lowbridge (1978), supra. These analogs were designed by replacing the two hydrogens on the $\beta$-carbon at the 1-position of the highly active and selective antidiuretic peptide 1-deamino[4-valine, 8-D-arginine] vasopressin (dVDAVP), Manning et al., J. Med. Chem., vol. 16 (1973) at 975, by two methyl groups and a cyclopentamethylene group, respectively. These substituents had previously been shown to convert the highly potent oxytocic agonist 1-deamino-oxytocin (dOT) into potent antagonists of the oxytocic response to oxytocin, specifically, [1-deaminopenicillamine] oxytocin (dPOT) and [1-($\beta$-mercapto-$\beta$,$\beta$-cyclopentamethylenepropionic acid)] oxytocin (d(CH$_2$)$_5$OT). See, Hope et al., J. Biol. Chem., vol. 237 (1962) at 1563, Schulz et al., J. Med. Chem., vol. 9 (1966) at 647 and Nestor et al., J. Med. Chem., vol. 18 (1975) at 284.

The discovery of the antidiuretic antagonists d(CH$_2$)$_5$Tyr(alk)VAVP, Sawyer, et al., (1981), supra, Manning et al., (1981) supra, led to the synthesis of other position two substituted analogs. Enhanced antidiuretic potencies were exhibited by the various O-alkyl D-tyrosine analogs, Manning et al., in Peptides, Structure, Function, Dan H. Rich and E. Gross, eds., Pierce Chemical Co (in press) and J. Med. Chem. (in press). The unalkylated D-tyrosine isomers of d(CH$_2$)$_5$ VDAVP and d(CH$_2$)$_5$VAVP, i.e., d(CH$_2$)$_5$D-Tyr-VDAVP and d(CH$_2$)$_5$D-Tyr-VAVP were also shown to be anti-antidiuretics. Attempts to further enhance anti-antidiuretic potency and selectivity have led to the synthesis of analogs of d(CH$_2$)$_5$D-Tyr$^2$VAVP and d(CH$_2$)$_5$D-Tyr$^2$VDAVP containing other D-amino acids in place of D-tyrosine at position two, in accordance with the present invention.

It was found, in accordance with the present invention, that some d(CH$_2$)$_5$VAVP derivatives having a D-amino acid other than tyrosine and larger than alanine in the 2-position are more potent antagonists of the antidiuretic action of AVP than compounds having D- or L-tyrosine ether units or a D-tyrosine unit at the 2-position of d(CH$_2$)$_5$VAVP or d(CH$_2$)$_5$VDAVP.

Preferred compounds of this invention are those wherein the 8-substituent is Arg and the 2-substituent is D-Phe, D-Val, D-Leu and D-Ile.

As shown by intravenous administration of the compounds of the invention to hydrated rats anesthetized with ethanol, compounds having D-Phe, D-Val, D-Leu or D-Ile substituents at the 2-position have high pA$_2$ values and effective doses near or lower than the lowest effective doses known heretofore.

Compounds having D-Phe, D-Val, D-Leu or D-Ile at the 2-position and Arg at the 8-position are also pure antidiuretic antagonists, i.e., these compounds have no transient antidiuretic agonism. Moreover, these compounds are more selective in their activity, by virtue of high anti-ADH/antivasopressor activity ratios, than known compounds.

The compounds of this invention are very effective antagonists of the antidiuretic response to ADH. They can therefore be used in pharmacological studies on the contribution of ADH to a variety of pathological states involving water retention. It is further contemplated that they could be effective and specific agents for treating the syndrome of inappropriate secretion of ADH, that is, the Schwartz-Bartter syndrome or SIADH. This syndrome can complicate a number of disorders, including carcinomas, pulmonary diseases, intracranial diseases and head injuries, Bartter et al., Am. J. Med., vol. 42 (1967) at 790.

The compounds of this invention can be employed in mixture with conventional excipients, i.e., physiologically and pharmaceutically acceptable organic or inorganic carriers suitable for parenteral or enteral application, which do not interact deleteriously with the active compounds.

Suitable pharmaceutically acceptable carriers include, but are not limited to, water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral or intranasal application, solutions, preferably aqueous solutions, as well as suspensions, emulsions, or implants, including suppositories, are particularly suitable. Ampoules are convenient unit dosages.

The compounds of this invention are generally administered to animals, including but not limited to mammals, e.g., livestock, household pets, humans, cattle, cats and dogs. A diuretically effective daily dosage of the active compounds can be administered parenterally in a single dosage or as divided dosages throughout the day.

Parenteral or intranasal administration is preferred, the compounds of Formula I of this invention being particularly valuable in the treatment of humans afflicted with water retention of any etiology. In this regard, they can be administered in substantially the same manner as the known compounds oxytocin and vasopressin, to achieve their physiological effects.

It will be appreciated that the actual preferred amounts of active compounds used will vary according to the specific compound being utilized, the particular compositions formulated, the mode of application, and the particular organism being treated. Optimal application rates under/in a given set of conditions can be ascertained by those skilled in the art of using conventional dosage determination tests in view of the above guidelines.

DESCRIPTION OF PREFERRED EMBODIMENT

Preferred antidiuretic antagonists of the invention are compounds of Formula I, wherein X is D-Phe, D-Val, D-Leu or D-Ile and Z is L-Arg. The D-Ile or D-Phe compound is most preferred.

Without further elaboration, it is believed that one skilled in the art can, using the preceding description, utilize the present invention to its fullest extent. The following specific embodiments are, therefore, to be construed as merely illustrative and not limitative of the remainder of the disclosure in any way whatsoever. In the following Examples, the temperatures are set forth uncorrected in degrees Celsius. Unless otherwise indicated, all parts and percentages are by weight.

Chloromethylated resin (Bio-Rad Bio-Beads SX-1) was esterified by the procedure of Gisin, *Helv. Chim. Acta.*, vol. 56 (1973) at 1476 with Boc-Gly until 0.47 mmol/g and ~0.64 mmol/g were incorporated. Amino acid derivatives including Boc-Tyr(Me) ($R_f$(A) 0.7; $R_f$(B) 0.8) were supplied by Bachem Inc., or synthesized.

Triethylamine (TEA) and N-methylmorpholine (NMM) were distilled from ninhydrin.

Acetic acid used as the HCl-acetic acid cleavage reagent was heated under reflux with boron triacetate and distilled from the reagent. Dimethylformamide (DMF) was distilled under reduced pressure immediately before use. Methanol was dried with magnesium methoxide and distilled. Other solvents and reagents were analytical grade.

Thin layer chromatography (TLC) done on silica gel plates (0.25 mm, Brinkmann Silplate) using the following solvent systems: A. cyclohexane-chloroform-acetic acid (2:8:1 v/v); B. propan-1-ol-ammonia (34%) (2:1 v/v); C. ethanol (95%)-ammonia (34%) (3:1 v/v); D. chloroform-methanol 7:3 v/v; E. butan-1-ol-acetic acid-water (4:1:5 v/v, upper phase); F. butan-1-ol-acetic acid-water-pyridine (15:3:3:10 v/v). The applied loadings were 10–50 μg. The minimum length of the chromatograms was 10 cm. Chloroplatinate reagent and iodine vapor were used for development of the chromatograms.

Amino acid analysis of the peptides was done by the method of Spackman et al., *Anal. Cheml.* vol. 30 (1958) at 1190, in which peptide samples weighing about 0.5 mg were hydrolyzed with constant boiling hydrochloric acid (400 μl) in evacuated and sealed ampules for 18 h at 120° C. The analyses were performed using a Beckman Automatic Amino Acid Analyzer, Model 121. Molar ratios were referred to Gly=1.00. Elemental analyses were performed by Galbraith Laboratories, Inc. Knoxville, Tenn. The analytical results for the elements indicated by their respective symbols were within ±0.4% of theoretical values. Optical rotations were measured with a Bellingham Stanley, Ltd., Model A polarimeter, type pl.

EXAMPLE 1

β-(S-Benzylmercapto)-β,β-cyclopentamethylenepropionyl-Tyr(Me)-Phe-Gln-Asn-Cys(Bzl)-Pro-Arg(Tos)-Gly-NH₂

(a) Combination of Solid Phase and Solution Methods

Boc-Tyr(Me)-Phe-Gln-Asn-Cys(Bzl)-Pro-Arg(Tos)-Gly-NH₂, prepared by the method of Bankowski et al., *J. Med. Chem.*, vol. 21 (1978) at 850 (319 mg, 0.26 mmol), was dissolved in TEA (6.5 ml) and stirred at room temperature for 40 mins. Cold ether (20 ml) was added to produce a precipitate which was filtered and washed with ether (5×10 ml). The product was dried in vacuo over sodium hydroxide pellets. This material (318.5 mg) was dissolved in DMF (0.8 ml), to which was added N-methylmorpholine (10 μl). The resulting solution had a pH of 7–8, measured with moist pH paper. After this neutralized solution was stirred at room temperature for 30 mins, a solution of p-nitrophenyl β-(S-benzyl-mercapto)-β,β-cyclopentamethylenepropionate, Nestor et al., *J. Med. Chem.*, vol. 18 (1975) at 284, (445 mg, 1.155 mmol in 0.4 ml of DMF) was added. The reaction mixture was stirred at room temperature. After 72 hours' stirring, TLC analysis using system D showed that the reaction mixture still contained a trace of the free octapeptide amide. N-Hydroxybenzotriazole monohydrate, Konig et al., *Chem. Ber.*, vol. 103 (1970) at 788, (39.3 mg, 0.26 mmol) was added. Coupling was complete within 5 hours. The precipitate was filtered, washed with cold ethyl acetate (4×10 ml) and dried in vacuo. The crude product (339 mg) was twice reprecipitated from DMF-methanol to give the acylpeptide amide (295.2 mg, 77.3%): mp. 209°–211° C.; $[\alpha]_D^{24} = -43.6°$ (C 0.5, DMF); $R_f$(E) 0.45, $R_f$(F) 0.63 Anal. ($C_{73}H_{94}O_{14}N_{14}S_3$) C, H, N.

Amino acid analysis: Tyr, 0.80; Phe, 1.01; Glu, 1.04; Asp, 1.02; Cys(Bzl), 0.98; Pro, 1.06; Arg, 1.01; Gly, 1.00; NH₃ 2.91.

(b) Total Synthesis on Resin

Boc-Tyr(Me)-Phe-Gln-Asn-Cys(Bzl)-Pro-Arg(Tos)-Gly-resin (1.11 g, 0.4 mmol prepared from Boc-Gly-resin using solid phase methodology) was converted to the acyloctapeptide resin (1.167 g, weight gain 57 mg, 97.6% of theory) in one cycle of deprotection, neutralization and coupling with p-nitrophenyl β-(S-benzyl-mercapto)-β,β-cyclopentamethylenepropionate, see Nestor supra. The resin was ammonolyzed, Manning, *J. Am. Chem. Soc.*, vol. 90 (1968) at 1348. The product was extracted with dimethylformamide (DMF). After the solvent was evaporated in vacuo, the residue was precipitated by addition of water. The crude product (410 mg) was twice reprecipitated from DMF-ethanol to give the acyloctapeptide (302 mg, 50.7% based upon initial glycine content of the resin); mp. 206°–208° C. (decomp); $R_f(E)$ 0.45, $R_f(F)$ 0.63; $[\alpha]_D^{24} = -43.1°$ (C 1, DMF). Anal. ($C_{73}H_{94}N_{14}O_{14}S_3$) C, H, N.

Amino acid analysis: Tyr, 0.79; Phe, 1.01; Glu, 1.03; Asp, 1.04; Cys(Bzl), 0.97; Pro, 1.03; Arg, 0.99; Gly, 1.00; NH₃, 2.95.

EXAMPLE 2

β-(S-Benzylmercapto)-β,β-cyclopentamethylenepropionyl-Tyr(Bzl)-Phe-Gln-Asn-Cys(Bzl)-Pro-Arg(Tos)-Gly-NH₂

Boc-Tyr(Bzl)-Phe-Gln-Asn-Cys(Bzl)-Pro-Arg(Tos)-Gly-resin (1.46 g, 0.5 mmol) was converted to acyloctapeptide resin (1.55 g, weight gain 70 mg, 95.9% of theory) as in Example 1 by one cycle of deprotection, neutralization and coupling with p-nitrophenyl β-(S-benzylmercapto)-β,β-cyclopentamethylenepropionate. The product obtained by ammonolysis of the resin was extracted with DMF. The solvent was evaporated in vacuo and the residue was precipitated by addition of water. The crude product (723 mg) was reprecipitated from DMF-ethanol and DMF-2% aqueous AcOH. (488 mg; 62.4% based on initial Gly content on the resin); mp. 183°–185° C.; $R_f(E)$ 0.38; $R_f(D)$ 0.41; $[\alpha]_D^{23} = -32.9°$ (C 1 DMF). Anal. ($C_{79}H_{98}N_{14}O_{14}S_3$) C, H, N.

Amino acid analysis: Tyr, 0.97; Phe, 1.02; Glu, 1.05; Asp, 1.01; Cys(Bzl), 0.98; Pro, 1.04; Arg, 0.98; Gly, 1.00; NH₃.

EXAMPLE 3

[1-(β-Mercapto-β,β-cyclopentamethylenepropionic acid), 2-(O-methyl)tyrosine]-arginine vasopressin (a) From Nonapeptide Amide A solution of the protected nonapeptide amide, prepared as in Example 1, (170 mg, 0.114 mmol) in 400 ml of ammonia (dried over sodium and redistilled) was stirred at the boiling point with sodium from a stick of the metal contained in a small bore glass tube until a light blue color persisted in the solution for 30 sec, in accordance with duVigneaud, *J. Am. Chem. Soc.*, vol 76 (1954) at 3115. Dry glacial acetic acid (0.4 ml) was added to discharge the color. The solution was evaporated. A solution of the residue in aqueous acetic acid (0.2%; 800 ml), was treated with 2 M ammonium hydroxide solution to give a solution of pH 7.5. To this stirred solution was added gradually an excess of a solution of potassium ferricyanide (0.01 M, 11.4 ml), Hope et al., *J. Biol. Chem.*, vol. 237 (1962) at 1563. The yellow solution was stirred for 90 min more and for 1 h with anion-exchange resin (BioRad AG-3, Cl⁻ form, 10 g damp weight). The suspension was filtered slowly through a bed of resin (80 g damp weight). The resin bed was washed with 300 ml of aqueous 0.2% acetic acid and the combined filtrate and washings were lyophylized. The resulting powder (1386 mg) was desalted on a Sephadex G-15 column (110×2.7 cm) and eluted with aqueous acetic acid (50%) at a flow rate of 4 ml/h by the technique of Manning et al., *J. Chromatog.*, vol. 38 (1968) at 396. The eluate was fractioned and monitored for absorbance of 280 nm. The fractions comprising the major peak were pooled and lyophylized. The residue (55.5 mg) was further subjected to gel filtration on a Sephadex G-15 column (100×1.5 cm) and eluted with aqueous acetic acid (0.2 M) at a flow rate of 2.5 ml/h. The peptide was eluted in a single peak (absorbance 280 nm). Lyophilization of the pertinent fractions yielded the vasopressin analog (49 mg, 37.3%) $R_f(E)$ 0.19; $R_f(F)$ 0.30; $[\alpha]_D^{22} = -59.6$ (C 0.19, 1 M AcOH).

Amino acid analysis: Tyr, 0.81; Phe, 1.01; Glu, 1.04; Asp, 0.98; Pro, 1.04; Arg, 0.95; Gly, 1.00; NH₃, 3.10. Analysis following performic acid oxidation prior to hydrolysis according to Moore, *J. Biol. Chem.*, vol. 238 (1963) at 235, gave a Cys(O₃H)-Gly ratio of 1.03:1.00.

(b) From Acyloctapeptide

Treatment of the acyloctapeptide (160 mg, 0.107 mmol) as described in Example 3 (a) yielded the analog (64 mg, 51.7%), which was indistinguishable from the foregoing preparation by TLC: $[\alpha]_D^{23} = -59.1°$ (C 0.5, 1 M AcOH).

Amino acid analysis: Tyr, 0.80; Phe, 1.02; Glu, 1.02; Asp, 0.98; Pro, 1.03; Arg, 0.96; Gly, 1.00; NH₃, 3.05. Analysis following performic acid oxidation prior to hydrolysis gave a Cys-(O₃H)-Gly ratio of 1.02:1.00.

EXAMPLE 4

[1-(β-Mercapto-β,β-cyclopentamethylenepropionic acid] arginine vasopressin

Treatment of the acyloctapeptide (173 mg, 0.111 mmol) as described in Example 3 (a) yielded the analog (66 mg, 52%) $R_f(E)$ 0.19, $R_f(F)$ 0.43; $[\alpha]_D^{23} = -58.7°$ (C 0.5, 1 M AcOH).

Amino acid analysis: Tyr, 0.96; Phe, 0.98; Glu, 1.01; Asp, 1.01; Pro, 1.05; Gly, 1.00; NH₃, 2.95. Analysis following performic acid oxidation prior to hydrolysis gave a Cys(O₃H)-Gly ratio of 1.01:1.00.

EXAMPLE 5

[1-(β-Mercapto-β,β-cyclopentamethylenepropionic acid), 2-substituted, 4-valine]-(L- and D-)-arginine vasopressin Compounds of this series were prepared by solid-phase synthesis, modified as in Manning et al., *J. Med. Chem.*, vol. 16 (1973) at 975, Kruszynski et al., *J. Med. Chem.*, vol. 23 (1980) at 364 Manning et al. *J. Med. Chem.*, vol. 24 (1981) at 701, to obtain protected intermediates for each analog. The procedures of Bodanszky et al., *J. Am. Chem. Soc.*, vol. 81 (1959) at 5688 and *J. Org. Chem.*, vol. 39 (1974) at 444, employing a p-nitrophenyl ester, facilitated by the use of hydroxybenzotriazole (Konig et al., supra), were used for the coupling of β-(S-benzylmercapto)-β,β-cyclopentamethylenepropionic acid in accordance with Nestor, supra, to obtain precursor compounds. Each precursor was deblocked (duVigneaud, supra) with sodium in liquid ammonia. The resulting disulfhydryl compounds were oxidatively cyclized with potassium ferricyanide (Hope et al., supra). The analogs were desalted and purified by gel filtration on Sephadex G-15 by a two step procedure using 50% acetic acid and 0.2 M acetic acid, respectively, as eluants. The purity and identity of each analog was ascertained by thin-layer chromatography in two different solvent systems, Kruszynski et al., *J. Med. Chem.*, vol. 23 (1980) at 364, or by amino acid analysis as above.

Compounds of Formula I, or related to Formula I, prepared by the foregoing procedure were assayed by TLC on silica gel in two solvent systems: E. butanol/a- cetic acid/water (BAW) (4:1:5) or F. butanol/acetic acid/water/pyridine (15:3:3:10). Results were:

| X | Z | R$_f$(E) | R$_f$(F) |
|---|---|---|---|
| D-Tyr | L-Arg | 0.17 | 0.50 |
| D-Phe | L-Arg | 0.17 | 0.52 |
| Gly | L-Arg | 0.15 | 0.48 |
| D-Ala | L-Arg | 0.16 | 0.49 |
| D-Val | L-Arg | 0.17 | 0.49 |
| D-Leu | L-Arg | 0.17 | 0.53 |
| D-Ile | L-Arg | 0.17 | 0.51 |
| D-Arg | L-Arg | 0.08 | 0.30 |
| D-Phe | D-Arg | 0.16 | 0.51 |

EXAMPLE 6

Antagonism to the vasopressor response was estimated in accordance with Dyckes et al., *J. Med. Chem.*, vol. 17 (1974) at 969. The values are expressed as pA$_2$ values, defined by Schild et al., *Br. J. Pharmacol.*, vol. 2 (1947) at 189.

Activity as antidiuretic agonists was determined by intravenous injection of compounds being evaluated into ethanol-anesthesized water-loaded rats in accordance with Sawyer et al., *Endocrinology*, vol. 63 (1958) at 694.

Antagonistic potencies were determined and expressed as "effective doses" and as pA$_2$ values. The "effective dose" is defined as the dose (in nanomoles per kilogram) that reduces the response seen from 2x units of agonist injected 20 min after the dose of antagonist to the response with 1x units of agonist. Estimated in vivo "pA$_2$" values represent the negative logarithms of the effective doses divided by the estimated volume of distribution (67 mL/kg). Results are given in Table 1.

Whereas [1-(β-mercapto-β,β-cyclopentamethylenepropionic acid), 2-(O-alkyl)tyrosine, 4-valine, 8-(L- and D-)arginine] vasopressin compounds were weak antidiuretic agonists, causing an initial submaximal inhibition of urine flow lasting about 10 min, followed by a period of inhibition of responses to ADH lasting 1 to 3 h, the preferred compounds of this invention, indicated by asterisks in the table below, had no antidiuretic agonistic activity.

The preferred compounds of this invention are also more selective than prior art antidiuretic antagonists with respect to antivasopressor potencies, as shown by the ratios of antivasopressor/anti-antidiuretic effective doses:

| Compounds | ED's $\frac{\text{Antivasopressor}}{\text{Anti-antidiuretic}}$ |
|---|---|
| d(CH$_2$)$_5$D-Tyr(Et) VAVP | 0.41 |
| d(CH$_2$)$_5$D-Phe VAVP | 0.87 |
| d(CH$_2$)$_5$[D-Val$^2$] VAVP | 12 |
| d(CH$_2$)$_5$[D-Leu$^2$] VAVP | 22 |
| d(CH$_2$)$_5$[D-Ile$^2$] VAVP | 12 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

TABLE 1

| Compound | Anti-Antidiuretic ED nmoles/Kg | pA$_2$ | Antivasopressor ED nmoles/Kg | pA$_2$ |
|---|---|---|---|---|
| d(CH$_2$)$_5$D-Tyr VAVP | 2.2 ± 0.2 | 7.51 ± 0.08(4) | 0.29 ± 0.09 | 8.41 ± 0.11(4) |
| d(CH$_2$)$_5$D-Phe VAVP | 0.67 ± 0.13* | 8.07 ± 0.09(8) | 0.58 ± 0.04 | 8.06 ± 0.03(4) |
| d(CH$_2$)$_5$[Gly$^2$] VAVP | agonist | — | agonist | — |
| d(CH$_2$)$_5$[D-Ala$^2$] VAVP | agonist | — | 172 ± 31 | 5.79 ± 0.08(4) |
| d(CH$_2$)$_5$[D-Val$^2$] VAVP | 2.3 ± 0.3* | 7.48 ± 0.06(4) | 27 ± 3 | 6.41 ± 0.05(4) |
| d(CH$_2$)$_5$[D-Leu$^2$] VAVP | 1.2 ± 0.3* | 7.79 ± 0.12(4) | 26 ± 5 | 6.45 ± 0.09(4) |
| d(CH$_2$)$_5$[D-Ile$^2$] VAVP | 0.70 ± 0.0* | 7.98 ± 0.05(4) | 8.2 ± 1.4 | 6.94 ± 0.08(5) |
| d(CH$_2$)$_5$[D-Arg$^2$] VAVP | >90 | <5.9 | ~260 | ~5.4 |
| d(CH$_2$)$_5$D-Phe VDAVP | 6.9 ± 1.3 | 7.07 ± 0.10(9) | 0.73 | 7.98 ± 0.07(4) |
| d(CH$_2$)$_5$Tyr(Me) VDAVP | 15 ± 3 | 6.68 ± 0.11(4) | 0.28 ± 0.05 | 8.44 ± 0.07(8) |
| d(CH$_2$)$_5$Tyr(Et) VDAVP | 5.7 ± 0.5 | 7.10 ± 0.08(4) | 0.34 ± 0.04 | 8.31 ± 0.05(8) |
| d(CH$_2$)$_5$Tyr(i-Pr) VDAVP | 8.5 ± 0.17 | 6.88 ± 0.07(4) | 0.28 ± 0.07 | 8.41 ± 0.08(8) |
| d(CH$_2$)$_5$Tyr(n-Pr) VDAVP | 14 ± 2 | 6.67 ± 0.05(4) | 1.1 ± 0.2 | 7.86 ± 0.10(8) |
| d(CH$_2$)$_5$Tyr(Me) VAVP | 3.1 ± 0.4 | 7.35 ± 0.06(4) | 0.29 ± 0.06 | 8.32 ± 0.08(4) |
| d(CH$_2$)$_5$Tyr(Et) VAVP | 1.9 ± 0.2 | 7.57 ± 0.06(4) | 0.49 ± 0.11 | 8.16 ± 0.09(4) |
| d(CH$_2$)$_5$Tyr(i-Pr) VAVP | 3.6 ± 0.9 | 7.32 ± 0.06(6) | 0.31 ± 0.06 | 8.36 ± 0.09(4) |
| d(CH$_2$)$_5$Tyr(n-Pr) VAVP | 3.5 ± 0.06 | 7.29 ± 0.07(4) | 0.40 ± 0.04 | 8.22 ± 0.04(4) |
| d(CH$_2$)$_5$—D-Tyr(Me) VAVP | 1.2 ± 0.3 | 7.77 ± 0.07(6) | 0.23 ± 0.04 | 8.48 ± 0.08(4) |
| d(CH$_2$)$_5$—D-Tyr(Et) VAVP | 1.1 ± 0.2 | 7.81 ± 0.07(5) | 0.45 ± 0.11 | 8.22 ± 0.12(4) |

What is claimed is:

1. A compound of the formula

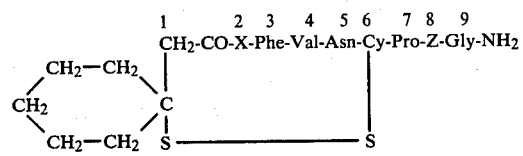

wherein X is D-Phe, D-Val, D-Leu, D-Ile, D-Arg, D-norvaline, D-norleucine, D-cyclohexylalanine, D-α-aminobutyric acid, D-threonine or D-methionine and Z is D- or L-Arg.

2. A compound of claim 1, wherein X is D-Phe, D-Val, D-Leu or D-Ile.

3. A compound of claim 1, wherein Z is L-Arg.

4. [1-(β-Mercapto-β,β-cyclopentamethylenepropionic acid), 2-D-phenylalanine, 4-valine]-arginine vasopressin, a compound of claim 1.

5. [1-(β-Mercapto-β,β-cyclopentamethylenepropionic acid), 2-D-valine, 4-valine]-arginine vasopressin, a compound of claim 1.

6. [1-(β-Mercapto-β,β-cyclopentamethylenepropionic acid), 2-D-leucine, 4-valine]-arginine vasopressin, a compound of claim 1.

7. [1-(β-Mercapto-β,β-cyclopentamethylenepropionic acid), 2-D-isoleucine, 4-valine]-arginine vasopressin, a compound of claim 1.

8. [1-(β-Mercapto-β,β-cyclopentamethylenepropionic acid), 2-D-phenylalanine, 4-valine, 8-D-arginine] vasopressin, a compound of claim 1.

9. A method for antagonizing the in vivo response of an animal to the antidiuretic action of an antidiuretic hormone, comprising administering to the animal being treated an amount of a compound of claim 1, in admixture with a physiologically and pharmaceutically acceptable carrier, effective to antagonize the antidiuretic response to the antidiuretic hormone.

10. The method of claim 9, wherein the antiduretic hormone is arginine vasopressin.

11. The method of claim 9, wherein the compound is administered parenterally.

12. A method for antagonizing the in vivo response of an animal to the antidiuretic action of an antidiuretic hormone, comprising administering to the animal being treated an amount of the compound of claim 7, in admixture with a physiologically and pharmaceutically acceptable carrier, effective to antagonize the antidiuretic response to the antidiuretic hormone.

13. A method for antagonizing the in vivo response of an animal to the antidiuretic action of an antidiuretic hormone, comprising administering to the animal being treated an amount of the compound of claim 4, in admixture with a physiologically and pharmaceutically acceptable carrier, effective to antagonize the antidiuretic response to the antidiuretic hormone.

* * * * *